United States Patent [19]

Daviduk et al.

[11] 4,238,631
[45] Dec. 9, 1980

[54] FLUID ZEOLITE CATALYZED CONVERSION OF ALCOHOLS AND OXYGENATED DERIVATIVES TO HYDROCARBONS BY CONTROLLING EXOTHERMIC REACTION HEAT

[75] Inventors: Nicholas Daviduk, Pennington; James H. Haddad, Princeton Junction, both of N.J.

[73] Assignee: Mobil Oil Corporation, New York, N.Y.

[21] Appl. No.: 89,706

[22] Filed: Oct. 30, 1979

[51] Int. Cl.³ .............................................. C07C 1/20
[52] U.S. Cl. .................................. 585/469; 585/639; 585/733
[58] Field of Search .................... 585/469, 639, 733

[56] References Cited

U.S. PATENT DOCUMENTS

| | | | |
|---|---|---|---|
| 3,998,898 | 12/1976 | Chang et al. | 585/469 |
| 3,998,899 | 12/1976 | Daviduk et al. | 585/469 |
| 4,071,573 | 1/1978 | Owen et al. | 585/469 |

Primary Examiner—Veronica O'Keefe
Attorney, Agent, or Firm—C. A. Huggett

[57] ABSTRACT

Alcohols and related oxygenates converted in a riser reactor and dense fluid catalyst bed (ZSM-5 cat) circulated through a plurality of satellite stripping-cooling zones for temperature control. Catalyst utilized comprises from 5 to 20 weight percent coke for activity and selectivity characteristics promoting the formation of olefins and aromatics at temperatures below 800° F.

8 Claims, 1 Drawing Figure

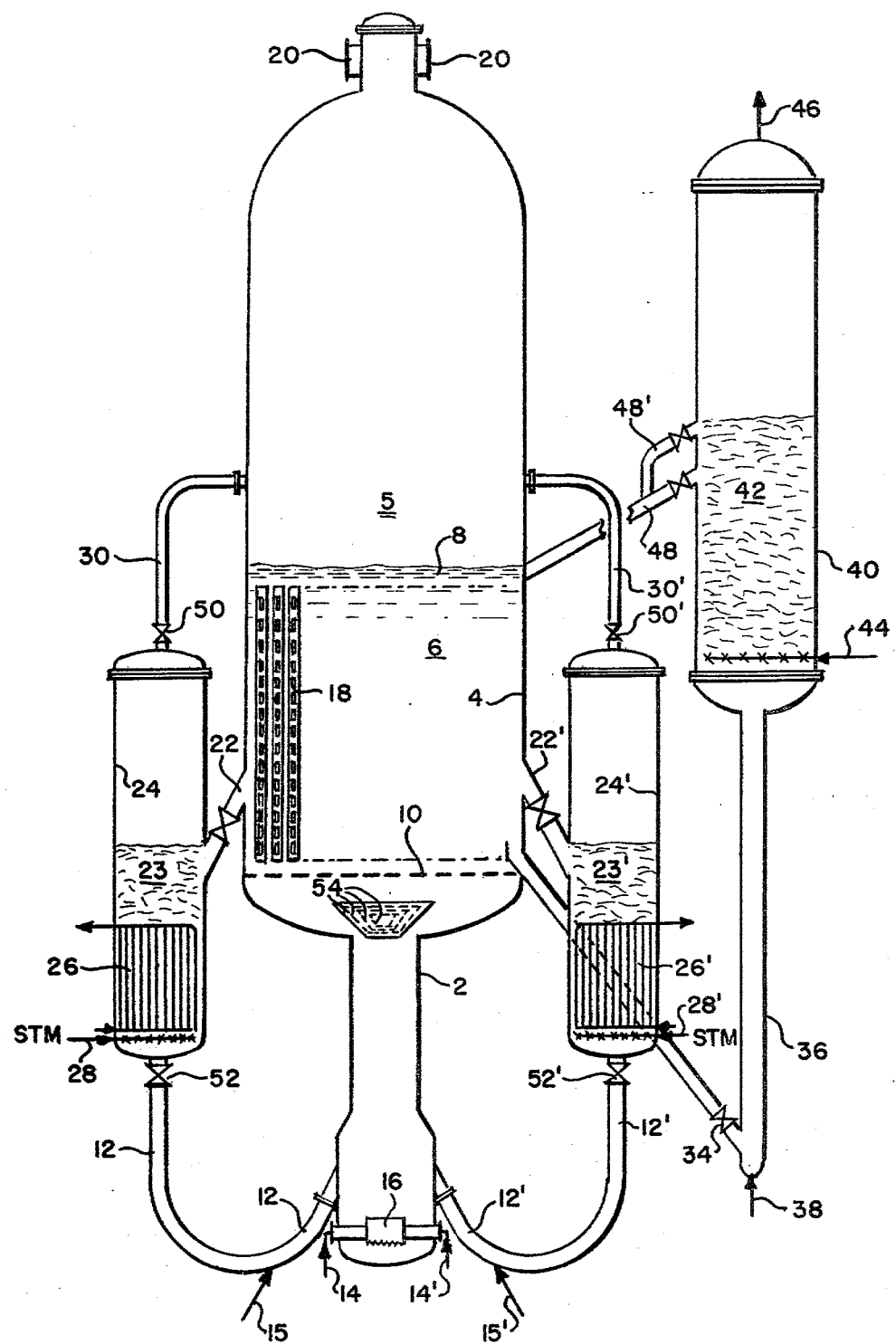

FLUID ZEOLITE CATALYZED CONVERSION OF ALCOHOLS AND OXYGENATED DERIVATIVES TO HYDROCARBONS BY CONTROLLING EXOTHERMIC REACTION HEAT

BACKGROUND OF THE INVENTION

The application of fluidized catalyst techniques developed particularly in the petroleum industry for effecting chemical reaction embodying the distribution of heat and/or the disposal of undesired heat has long been accepted as a major processing tool of the industry. For example, the catalytic cracking of oil vapors to produce lower boiling desired products and regeneration of the catalyst used in such an operation has been particularly useful for fluidized catalyst techniques. It has also been proposed to use the fluidized catalyst technique in the highly exothermic reactions of Fischer-Tropsch synthesis and the known Oxo process and other such exothermic processes primarly for the disposal of generated heat. In many of the fluidized catalyst operations developed, disposal of the reaction heat has been accomplished by many different techniques including transfer of catalyst through cooling sections and/or including indirect cooling means with liquids or a fluid catalyst to absorb reaction heat transferred directly or indirectly by the finely divided fluidized catalyst particles. Not only are these prior art catalyst techniques used for temperature control by addition and/or removal but it has also been found useful for maintaining selective conversions and extending the active life of the catalyst used in the process.

The present invention is concerned with an arrangement of apparatus and method of operation employing a fluid catalyst system in which methanol and related oxygenates are converted particularly to dimethyl ether and hydrocarbons in an upflowing catalyst phase system comprising relatively diluted and more dense phase systems. The exothermic heat of reaction is as herein after provided to provide desired product selectivity and prolong the useful life of the catalyst employed in the chemical conversion operation. U.S. patents considered in the preparation of this application include Nos. 2,373,008; 3,480,408; 3,969,426; 4,013,732; 4,035,430; 4,044,061; 4,046,825; 4,052,479; 4,071,573 and 4,118,431.

SUMMARY OF THE INVENTION

This invention relates to the method and means for effecting selective chemical reactions in the presence of a catalyst comprising a select class of particulate crystalline zeolites. More particularly, the present invention is concerned with effecting exothermic chemical reactions in the presence of crystalline zeolites of selected crystal arrangement particularly promoting the formulation of hydrocarbon product materials higher boiling than the reactant charge material. In a more particular aspect, the present invention is concerned with effecting the conversion of lower alcohols, related oxygenates and derivatives thereof in a fluidized mass of catalytic particulate material comprising a selected class of crystalline zeolite providing a pore dimension greater than about 5 Angstroms, pore windows of a size provided by 10-membered rings of oxygen atoms, a silica/alumina ratio of at least 12 and a constraint index in the range of 1 to 12. The present invention is concerned particularly with an arrangement of apparatus for effecting the catalytic conversion of alcohols and compounds of carbon and hydrogen with and without combined oxygen with a fluid mass of catalyst particles under temperature restricted conditions to achieve high yields of higher boiling hydrocarbons including gasoline boiling hydrocarbons.

The present invention is concerned with the conversion of methanol or a mixture of lower alcohols and related oxygenates such as ethers, aldehydes and ketones in the presence of a special zeolite catalyst represented by ZSM-5 zeolite maintained in a upflowing fluid condition comprising a dispersed catalyst phase riser contact zone discharging into a more dense upflowing fluid mass of catalyst particles. The alcohol containing feed initially charged in liquid and/or vaporous condition may be relatively pure methanol or comprise an ether derivative thereof as a part of the feed.

In the upwardly flowing dispersed catalyst phase portion of the conversion system maintained in a riser conversion zone under restricted exothermic temperature rise conversion conditions, it is contemplated employing a catalyst to feed weight ratio in the range of from 10 to 20/1 catalyst to feed weight ratio under velocity conditions promoting the catalyst flow reaction conditions herein described. The feed reaction-catalyst suspension initially formed is discharged into the bottom of a more dense upwardly flowing fluid mass of catalyst particles above a distributor grid above the riser outlet. The relationship of catalyst and reactant flow in the riser and more dense catalyst mass thereabove is maintained under temperature, pressure and space velocity conditions selected to particularly achieve greater than 95% conversion of a methanol reactant feed, and more preferably a conversion of at least 99 or 99.5% thereof to $C_1$ to $C_{10}$ hydrocarbons and water is desired. Thus, in the exothermic dispersed catalyst phase riser contact zone, it is contemplated employing a reactant velocity in the range of 15 to 40 feet per second.

In a particular operation of the apparatus of the invention, a vaporized methanol feed with or without related oxygenates is mixed with the special catalyst charged to the bottom of the riser contact zone as more particularly discussed below to form a suspension for flow upwardly through the riser. In this dispersed catalyst phase operation, it is desirable to restrict the catalyst temperature charged to the riser to a temperature of about 612° F. when employing a catalyst to feed ratio of 10 to 1 and, when employing the 20 to 1 ratio, the catalyst temperature is preferably restricted to about 690° F. The dispersed catalyst phase suspension is passed through a riser contact zone of at least 20 feet in length and more preferably from 25 feet up to about 70 feet in length before encountering a distributor grid across the bottom of a larger diameter more dense fluid mass of catalyst thereabove. In this arrangement, the reactant residence time in the riser will vary within the process restrictions herein identified. It is contemplated providing in the riser contact zone a residence time of 1 to 10 seconds. In the more dense phase of catalyst thereabove a reactant product residence time in contact with catalyst is within the range of 5 to 40 seconds. The exothermic operation contemplated within the above operating constraints, rely upon using a catalyst concentration within the riser contact zone within the range of 1 to 15 pounds per cubic foot and in the range of 20 to about 40 pounds per cubic foot in the more dense catalyst bed phase above the grid. A catalyst-reactant temperature rise restriction not to exceed more than about 195 degrees exothermic temperature rise is maintained between the riser suspension inlet and reactant product outlet above the dense fluid bed of catalyst. Thus the temperature constraints of the operation are selected to restrict the product outlet of the dense fluid bed of catalyst to below 800° F., and preferably the temperature is not substantially above 765° F. The pressure of the operation is maintained low and generally not above about 4 atmospheres pressures. It is preferred that the reactor pressure at the bottom of the dense bed be restricted to within the range of 2 to 2.5 gauges atmospheres.

These conditions allow the conversion of methanol with minimum contact of methanol with the final desired products. The reaction path for methanol conversion to hydrocarbons shows that very high space velocities within the range of 50 to 200 such as occurs in a dilute catalyst phase causes methanol to be converted to dimethyl ether and water. This conversion is about 70% completed before any significant quantities of aromatics are formed.

This initial methanol conversion step is important since methanol and aromatics readily combine to form tetramethylbenzene (durene) in greater than desirable quantities. This reaction would occur if methanol were injected directly into a fluid mass of catalyst characterized by good backmixing.

The desired hydrocarbon products preferably comprising $C_{10}$ and lower boiling materials are obtained usually at the low space velocities in the range of 0.5 to 3.0. This is the space velocity range within which the upper or dense catalyst phase bed is operated.

This invention apparatus causes a very large portion of the methanol feed to be converted into dimethylether and olefins in a dilute catalyst phase riser reactor prior to contact with significant quantities of higher boiling materials including aromatics and the remaining conversion thereof to desired hydrocarbons in the upper more dense catalyst phase of the reactor arrangement. By maintaining a high coke level on the catalyst, in the range of 10 to 20 weight percent coke on catalyst, thereby reducing the catalyst activity, olefins are preferentially produced for a given space velocity under selected temperature conditions. This method of operation prevents or substantially reduces the occurrence of reactions proceeding to the formation of substantial amounts of paraffins and aromatics and minimizes back mixing of methanol reactant with aromatic products. The high coke level is maintained by a limited regeneration of a portion of the catalyst recovered from the reaction zone. Generally speaking carbon buring can be limited by controlling the amount of oxygen available to burn the coke on the catalyst. Any technique suitable for the purpose may be employed.

The methanol conversion operation of this invention is one which requires and is designed to obtain substantial restriction of the reactant vapor bubble growth to low orders of magnitude and thus the vapor-catalyst hydraulic relationship in the contact zone is restricted by baffles, tubes or a combination thereof or by any other suitable apparatus means therein which will restrict the free space and provide surface area of the baffles equivalent to a hydraulic diameter not to exceed about 8 inches and preferably not more than about 4 inches. Bubble dispersing means in the catalyst contact zones and particularly the dense fluid bed catalyst contact zone may also be accomplished with some success with Pall type rings of desired relatively large size, vertically displaced baffle means such as honeycomb sections or portions thereof permitting transverse flow, sections of Glitsch grid, perforated pipe sections, and other known baffling means suitable for the purpose. It is particularly desirable however to use elongated open or closed end tubes vertically in the most dense fluid bed and perforated in the walls thereof to provide the surface area above identified and transverse flow of catalyst particles in suspension.

The dispersed catalyst phase riser reactor of this invention may be a single large diameter riser reactor tube, or a plurality of smaller diamter riser tubes such as 3 or 4 or more separate riser tubes bundled adjacent to one another or separated from one another, as desired, may be employed in place of the one riser tube. Charging catalyst and alcohol reactant in vapor form to the bottom of each riser reactor tube to form a suspension may be accomplished by one or more techniques known in the prior art to provide an upflowing suspension of desired particle concentration.

The crystalline aluminosilicate zeolites utilized herein are members of a novel class of zeolites that exhibits unusual properties. Although these zeolites have unusually low alumina contents, i.e. high silica to alumina ratios, they are very active even when the silica to alumina ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which, due to pore or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (C.I.) values for some typical crystalline aluminosilicates (CAS) zeolites are:

| CAS | C.I. |
| --- | --- |
| ZSM-5 | 8.3 |
| ZSM-11 | 8.7 |
| ZSM-12 | 2 |
| ZSM-35 | 4.5 |
| ZSM-38 | 2 |
| TMA Offretite | 3.7 |
| Beta | 0.6 |
| ZSM-4 | 0.5 |
| H-Zeolon (Mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. The preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.57 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5% by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely, with the zeolite content ranging from between about 1 to about 99% by weight and more usually in the range of about 5 to about 80% by weight of the dry composite.

The present invention is concerned with an arrangement of apparatus and the method of using catalyst of selected activity therein for effecting the exothermic conversion of hetero type compounds, ethers and carbonyl compounds with a fluid mass of catalyst particles in a manner particularly promoting and selecting the formation of olefinic, paraffinic, naphthenic and aromatic compounds. More particularly, the present invention is concerned with a method and systems employed for dispersing the exothermic heat of chemical reaction generated in the preparation of the above components and related compounds by contacting a fluidized catalyst comprising a ZSM-5 crystalline zeolite with one or more reactants selected from the group consisting of alcohols, ethers, carbonyl compounds, and mixtures thereof.

The drawing is a diagrammatic representation in elevation of one arrangement of apparatus for effecting the catalytic conversion of alcohols such as methanol, ether derivatives, and related oxygenates in a special fluid catalyst system to form hydrocarbons including gasoline boiling hydrocarbon and LPG products.

Referring now to the drawing by way of example, a reactor arrangement is shown comprising a lower riser section 2 in open communication with the bottom of a larger diameter vessel 4 containing a relatively dense fluid bed of catalyst 6 having an upper interface 8. A distributor grid 10 is positioned across the lower bottom portion of vessel 4 and above the outlet of riser 2. Riser section 2 may comprise more than one separate riser, as mentioned above. There may be a plurality of separate riser conduits within riser 2 such as two, three or four risers, each separately fed with reactant feed and catalyst. In the specific arrangement of the drawing a fluid suspension of catalyst in methanol vapors is formed in the bottom portion of riser 2. Catalyst is changed to the lower portion of riser 2 by "U" bend transfer conduits 12 and 12'. The feed is charged to the bottom of the riser by inlet means 14 and 14' communicating with an inverted pan 16 open in the bottom thereof. The vaporous feed thus introduced mixes with introduced catalyst to form a suspension thereafter passed through the riser. Catalyst mass 6 is filled with a plurality of vertical elongated tubes 18 provided with openings in the wall thereof to restrict bubble growth within the fluid catalyst bed 6 as herein provided.

In the arrangement of the drawing, a reactant material such as methanol or one comprising methanol and ether is charged in vaporous condition to the bottom of riser 2 by conduits 14 and 14' at a temperature of about 250° to about 500° F. for admixture with cooled and stripped recycled catalyst charged by conduits 12 and 12'. A suspension mix temperature in the range of 574° to 664° F. is formed with the temperature adjusted recycled catalyst and charged vaporous reactant for passage upwardly through the riser represented by riser 2 in essentially a dispersed catalyst phase condition within the range of 1 to 15 and preferably from 2 to 5 pounds catalyst per cubic foot. The upflowing suspension in the riser section is maintained under operating conditions to achieve at least 90% conversion of charged methanol or reactants in the feed before passing through distributor grid 10 and into the bottom of the more dense fluid mass of catalyst 6 thereabove. Completion of the reactions desired to obtain more than two carbon bonded hydrocarbons is accomplished within the dense fluid catalyst bed 6 so that at least 99.5% of methanol in the feed is converted to a hydrocarbon product comprising $C_1$ to gasoline boiling hydrocarbons without exceeding an upper temperature limit of about 750° F. to about 800° F. and preferably not above about 765° F. Cyclone separation equipment not shown is provided in the upper portion of vessel 4 to effect recovery of entrained catalyst particles from reaction products. Products of reaction are recovered from the vessel by conduits 20 for separation and recovery in downstream equipment not shown for the recovery of gasoline boiling range hydrocarbons.

Catalyst is withdrawn from a lower portion of bed 6 by conduits 22 and 22' for transfer and downflow through catalyst stripping and cooling chamber 24 and 24'. Baffles not shown may or may not be employed in an upper portion of chamber 24 and 24' and above indirect heat exchange means 26 and 26' providing high temperature steam positioned in a lower bottom portion of chamber 24 and 24'. Stripping gas such as steam and preferably recycle gas obtained from the process is charged to vessel 24 and 24' by conduit 28 and 28' respectively. The stripping gas is preferably introduced below heat exchange means 26 and 26' for stripping the catalyst cooled to a desired temperature and before withdrawal from the strippers. The stripping gas passes generally upwardly through vessels 24 and 24' countercurrent to downflowing catalyst for the recovery by displacement of strippable hydrocarbons and particularly aromatics from the catalyst at a controlled temperature suitable for recycle to riser 2. Stripped products and stripping gas are removed by conduit 30 and 30' for passage to the dispersed catalyst phase 5 of vessel 4 and removal after cyclone separation not shown with reaction products by conduit 20. The stripped catalyst essentially free of aromatics passes downwardly through steam developing indirect heat exchange means 26 and 26' during which time the catalyst temperature is reduced to a level suitable for charging to the base of riser 2 as above discussed and forming a suspension temperature in riser 2 as defined above. The partially cooled catalyst passes from the bottom of strippers 24 and 24' by conditions 12 and 12' communicating with the lower portion of riser 2 as "U" shaped catalyst transfer conduits.

A portion of the catalyst inventory above identified is withdrawn from a bottom portion of bed 6 into a catalyst withdrawal well provided in the vessel above grid 10 and thence by conduit 32 provided with flow control valve 34 for catalyst regeneration. Generally the volume of catalyst withdrawn by conduit 32 will be from about 5 to 10% per hour of the total catalyst in the system. The catalyst withdrawn by conduit 32 is passed to the base of a riser 36 wherein it is mixed with a transport gas or lift gas introduced by conduit 38. The lift gas may be an inert gas or it may be a gas mixture used to effect a partial regeneration of the catalyst by a partial removal of deposited coke. A suspension is thus formed in riser 36 and the suspension is passed upwardly through riser 36 into regeneration zone 40 containing a bed of partially regenerated catalyst 42. A regeneration gas of desired oxygen concentration may all be added to the bottom of riser 36 or it may be added to a bottom portion of bed 42 by conduit 44 and provided with a suitable distributing grid within vessel 40. A $CO_2$ rich gaseous product of the partial coke burning regeneration operation is recovered from zone 40 by conduit 46 after passing through cyclonic separating means normally housed in the upper portion of vessel 40 but not shown. Regeneration of the catalyst is accomplished at a relatively low restricted temperature generally not substantially above 900° F. and under conditions to achieve only a partial removal of coke or carbonaceous deposits rather than provide a clean burned catalyst for the reasons above expressed. Thus carrying significant levels of coke on the catalyst is used in this methanol conversion operation as a means for controlling catalyst activity and selectivity characteristics. Such coke retention levels include from 5 to 20% by weight of coke on catalyst. In view of the temperature restrictions in bed 6 of reactor 4, it is necessary to pass a relatively low temperature catalyst of high residual coke from regenerator 40 to catalyst bed 6 by conduit 48 and 48'. On the other hand, regenerated catalyst may be passed to stripper 24 for flow downwardly therethrough with catalyst passed thereto by conduit 22 and thus return to the circulating catalyst system.

The reactor system above described may comprise more than the two catalyst-stripping-cooling zones 24 and 24' shown. In fact, it is contemplated providing four of such catalyst stripping-cooling zone arrangements connected to riser reaction zone to control a commercial system within the limits herein defined.

For example, at a LHSV of 1.0 and 12% coke by weight on the catalyst, 7% $C_2$ to $C_5$ by weight olefins are produced. Lowering the coke level increases catalyst activity and at the same space velocity a lower proportion of $C_2$ to $C_5$'s would remain, that is, more olefins would be converted to aromatics and paraffins.

By maintaining high coke level to produce olefins allows the conversion of the formed $C_3$-$C_5$ olefins plus the isoparaffins produced in this process to be converted in a downstream alkylation unit into additional gasoline. This further conversion of olefins results in a higher 9–10RVP gasoline yield than if the olefins were allowed to be converted into low molecular weight LPG paraffins.

In the apparatus arrangement of this invention, the pressure in stripper-cooling chambers and thus the upper level of catalyst retained therein is controlled by gaseous stripping material withdrawal conduits 30 and 30' provided with pressure contact valves 50 and 50'. Thus the pressure at the bottom of the stripping-cooling chamber is equivalent to the pressure maintained in the dispersed catalyst phase of reactor chamber 4 plus the head of pressure developed by the dense bed of catalyst in vessel 4 through withdrawal conduit 22 or 22' and the dense bed of catalyst 23 and 23' extending downwardly through vessels 24 and 24'. Valves 52 and 52' are for the purpose of shutting off the flow of catalyst from the bottom of vessels 24 and 24'. Some additional head of pressure is developed in conduits 12 and 12' to at least the bottom of the "U" bend of the catalyst transfer conduit.

The flow of catalyst from the bottom of the "U" bend upwardly therein into the riser reactor 2 for admixture with reactant is controlled by charging gaseous material into the upflowing catalyst by conduits 15 and 15'. The gaseous material charged by conduits 15 and 15' may be inert to the reactions desired, may be hydrocarbon gaseous products of reaction or the gaseous material thus charged may be methanol comprising feed otherwise charged by conduits 14 and 14' to the riser.

It will be recognized by those skilled in the art that instead of employing "U" bend catalyst transfer conduit, one may use straight sloping standpipes communicating with the bottom of riser 2. In this arrangement, catalyst flow control valves will be located adjacent the bottom of the standpipe. In this embodiment, the methanol reactant will be charged to the bottom of the riser. This sloping standpipe riser arrangement with feed charged to the bottom of the riser will be similar to that shown for regenerating the catalyst employing standpipe 32, valve 34, riser 36 and gaseous material inlet 38. Of course, there will be a sloping standpipe from each stripping-cooling vessel communicating with the bottom section of the riser reactor.

The apparatus of the invention contemplate relatively high catalyst circulation rates through the stripping-cooling zones as well as through a plurality of cyclone separators in the upper dispersed catalyst phase of reactor vessel 4. Although not specifically shown, it is contemplated employing from 6 to 8 combinations of 3-stage cyclones to achieve separation of catalyst particles from reaction products. Separated catalyst will be returned to the lower bottom portion of bed 6 but above grid 10 by cyclone diplegs suitable for the purpose.

To facilitate distribution of the suspension across the bottom of grid 10 following traverse of riser section 2, a plurality of diverging conical shaped baffles 54 coaxially aligned with the riser and positioned within one another are provided above the riser outlet in the dish shaped bottom section of vessel 4. The distributed suspension passes through grid 10 and into the bed of catalyst for flow upwardly therethrough about the gas bubble restricting baffles 18 discussed above.

Having thus generally described the apparatus and its method of operation for upgrading methanol containing feeds and described specific embodiments in support thereof, it is to be understood that no undue restrictions are to be imposed by reasons thereof except as defined by the following claims.

We claim:

1. A method for converting reactants comprising lower alcohols and related oxygenates to $C_{10}$ and lower boiling carbon-hydrogen compounds including LPG and gasoline boiling components which comprises:

passing a suspension of vaporized reactant material and fluid catalyst particles comprising a special crystalline zeolite represented by ZSM-5 crystalline zeolite upwardly through a relatively dispersed catalyst phase riser contact zone for a time temperature and pressure suitable to achieve at least 70% conversion of methanol in the reactant feed;

passing the suspension comprising products of reaction upwardly through a relatively dense fluid mass of catalyst particles for a residence time and temperature sufficient to achieve a total conversion of methanol in the feed equivalent to at least 90% and produce simultaneously a product mixture of $C_1$ to $C_{10}$ hydrocarbons comprising paraffins, olefins and aromatics;

passing catalyst withdrawn from a lower portion of said relatively dense fluid mass of catalyst particles downwardly through a plurality of separate catalyst stripping-cooling zones of desired temperature restriction and thence to the riser reactor for admixture with charged vaporous reactant;

passing stripped products from the stripping-cooling zone into a dispersed phase of catalyst above said more dense fluid mass of catalyst and withdrawing reaction products separated from catalyst in said dispersed phase of catalyst from an upper portion of said reaction zone.

2. The method of claim 1 wherein the exothermic temperature rise of said conversion in said riser and said relatively dense fluid mass of catalyst is restricted to maintain a dispersed phase temperature above said dense fluid mass of not more than 800° F.

3. The method of claim 2 wherein said dispersed phase temperature is restricted not to exceed 765° F.

4. The method of claim 1 wherein the catalyst to reactant ratio of the initially formed suspension in the riser is within the range of 10–20 to 1.

5. The method of claim 1 wherein conversion of methanol in the reactant feed is at least 90% in the riser conversion zone before distribution in the relatively dense fluid mass of catalyst thereabove.

6. The method of claim 1 wherein the relatively dense fluid mass of catalyst is provided with vertically extending baffle means arranged to restrict the vaporous catalyst mixture passing upwardly therethrough to a hydraulic diameter within the range of 4 to 8.

7. The method of claim 1 wherein a portion of the circulated catalyst is withdrawn and subjected to partial regeneration and thereafter returned to the circulated catalyst to maintain residual coke on the circulated catalyst and catalyst charged to the riser in the range of from 5 to 20 weight percent coke on the catalyst.

8. The method of claim 1 wherein catalyst circulation through the riser, dense fluid mass of catalyst thereabove and the stripper-cooling zone is in response to reactant feed rate and the catalyst pressure at the base of a catalyst transfer zone in communication with said riser reaction zone.

* * * * *

UNITED STATES PATENT AND TRADEMARK OFFICE
CERTIFICATE OF CORRECTION

PATENT NO. : 4,238,631
DATED : December 9, 1980
INVENTOR(S) : Nicholas Daviduk and James H. Haddad It is certified that error appears in the above-identified patent and that said Letters Patent are hereby corrected as shown below:

Column 1, line 20, "primarly" should read --primarily--.

Column 3, line 51, "buring" should read --burning--.

Column 4, line 13, "diamter" should read --diameter--.

Column 6, line 17, insert --be-- after "may".

Column 9, line 12, "changed" should read --charged--.

Column 10, line 17, "conditions" should read --conduits--.

Signed and Sealed this

Twenty-first Day of April 1981

[SEAL]

Attest:

RENE D. TEGTMEYER

*Attesting Officer*     *Acting Commissioner of Patents and Trademarks*